(12) United States Patent
Barone

(10) Patent No.: US 9,579,031 B2
(45) Date of Patent: Feb. 28, 2017

(54) DEVICE FOR MEASURING ELECTROMYOGRAPHIC SIGNALS WITH HIGH RESOLUTION AND HIGH NUMBER CHANNELS

(71) Applicant: BITRON S.p.A., Grugliasco (IT)

(72) Inventor: Umberto Barone, Grugliasco (IT)

(73) Assignee: BITRON S.P.A., Grugliasco (IT)

( * ) Notice: Subject to any disclaimer, the term of this patent is extended or adjusted under 35 U.S.C. 154(b) by 371 days.

(21) Appl. No.: 14/388,626

(22) PCT Filed: Nov. 5, 2012

(86) PCT No.: PCT/IB2012/002233
§ 371 (c)(1),
(2) Date: Sep. 26, 2014

(87) PCT Pub. No.: WO2013/068804
PCT Pub. Date: May 16, 2013

(65) Prior Publication Data
US 2015/0045689 A1 Feb. 12, 2015

(30) Foreign Application Priority Data
Nov. 8, 2011 (IT) .............................. TO2011A1024

(51) Int. Cl.
*A61B 5/00* (2006.01)
*A61B 5/04* (2006.01)
(Continued)

(52) U.S. Cl.
CPC ........ *A61B 5/04004* (2013.01); *A61B 5/0002* (2013.01); *A61B 5/0004* (2013.01);
(Continued)

(58) Field of Classification Search
CPC ........... A61B 5/04; A61B 5/0488; A61B 5/05; A61B 5/053; A61B 5/04004; A61B 5/0002;
(Continued)

(56) References Cited

U.S. PATENT DOCUMENTS 7,479,911 B2* 1/2009 Chakrabartty ........ H03M 3/466
341/143
8,525,673 B2* 9/2013 Tran .................... G06F 19/3418
340/3.1
(Continued)

OTHER PUBLICATIONS

International Search Report for International Application No. PCT/IB2012/002233 mailed Feb. 1, 2013 (2 pages).
(Continued)

*Primary Examiner* — Max Hindenburg
(74) *Attorney, Agent, or Firm* — Merchant & Gould P.C.

(57) ABSTRACT

A device for measuring electromyographic signals 2 is adapted to receive, through multiple channels "C", electromyographic signals "EMG" sensed by a plurality of electrodes 3 arranged on a patient "P". The device 2 includes: a conditioning circuit 21; a conversion circuit 22; a transmission circuit 23 to transmit the digitalized signals to a central control unit 1; an external casing 20 to enclose the circuits (21, 22, 23). The conditioning circuit 21 can be assembled modularly by establishing a cascade connection of one or more conditioning circuits 21. The conversion circuit 22 can be assembled modularly by connecting in parallel one or more conversion circuits 22 to vary the number of channels "C" through which electromyographic signals "EMG" are received. The conditioning circuits 21 and the conversion circuits 22 overlap at least partially to limit the dimensions of the external casing 20, ensuring wearability on the patient "P".

16 Claims, 4 Drawing Sheets

(51) Int. Cl.
*A61B 5/0492* (2006.01)
*A61B 5/0488* (2006.01)

(52) U.S. Cl.
CPC .......... *A61B 5/0488* (2013.01); *A61B 5/0492* (2013.01); *A61B 5/6801* (2013.01); *A61B 2562/046* (2013.01)

(58) Field of Classification Search
CPC ... A61B 5/0004; A61B 5/0492; A61B 5/6801; A61B 2562/046
See application file for complete search history.

(56) References Cited

U.S. PATENT DOCUMENTS

| | | | |
|---|---|---|---|
| 8,578,082 B2 * | 11/2013 | Medina | A61B 5/0002 710/303 |
| 2002/0095097 A1 | 7/2002 | Drongelen | |
| 2011/0251512 A1 | 10/2011 | Fink et al. | |

OTHER PUBLICATIONS

Notification of Transmittal of the International Preliminary Report on Patentability, PCT/IB2012/002233, Oct. 30, 2013, 6 pages.

* cited by examiner

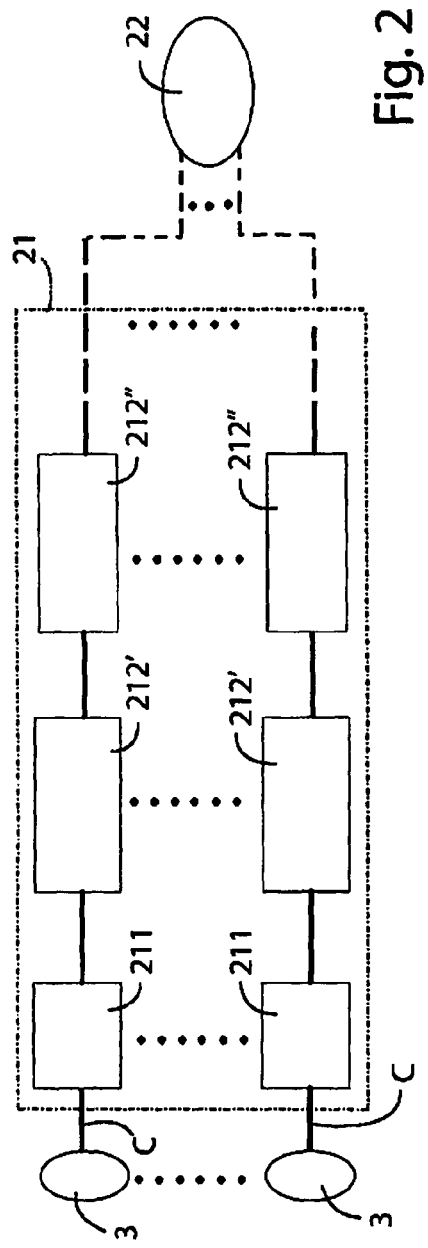
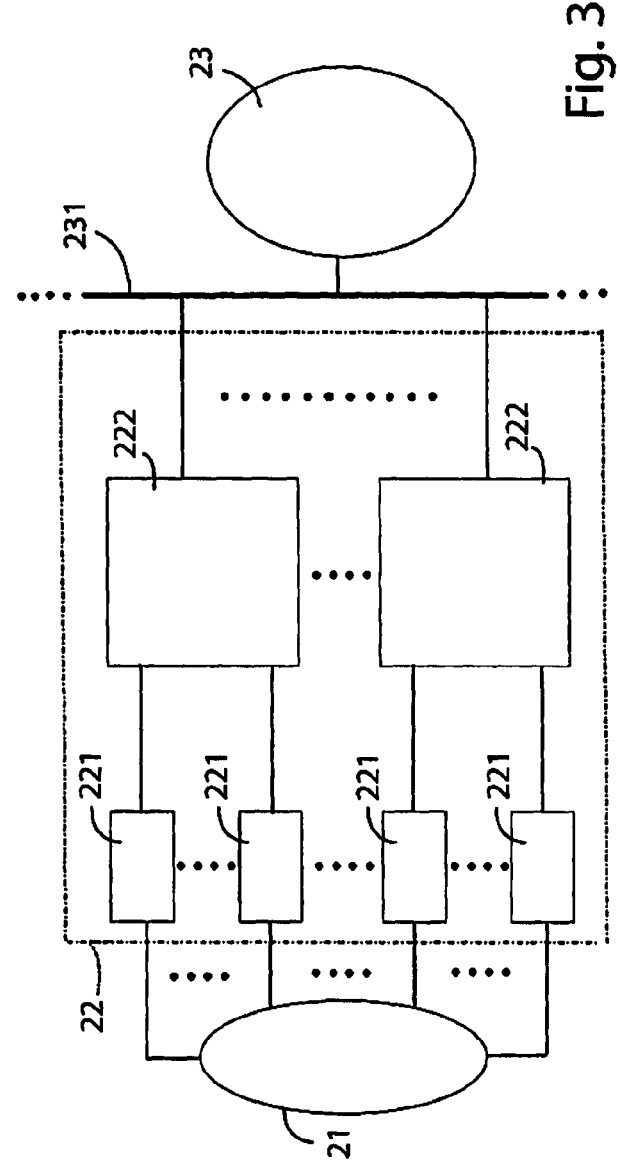
Fig. 2
Fig. 3

DEVICE FOR MEASURING ELECTROMYOGRAPHIC SIGNALS WITH HIGH RESOLUTION AND HIGH NUMBER CHANNELS

This application is a National Stage Application of PCT/IB2012/002233, filed 5 Nov. 2012, which claims benefit of Serial No. TO2011A001024, filed 8 Nov. 2011 in Italy and which applications are incorporated herein by reference. To the extent appropriate, a claim of priority is made to each of the above disclosed applications.

BACKGROUND

The present invention relates to a device for measuring electromyographic signals with high resolution and high number of channels, which device can be worn by the patient.

Measuring devices are known which can acquire electromyographic signals. Through a plurality of channels connected to as many electrodes, such devices can carry out measurements in order to determine various information about the propagation of such electromyographic signals.

Wearable measuring devices are also known, wherein the number of electrodes, and hence of channels, used for taking measurements does not exceed thirty-two.

Said devices can ensure high signal resolution, provided that the number of channels does not exceed the above-mentioned number.

Measuring devices are also known which can manage a plurality of electrodes which are more densely arranged on the human skin, with respect to the above-mentioned devices, such devices using up to two hundred and fifty-six channels. These devices cannot however ensure a high resolution of the measured signal. Such devices are large and must be located far from the patient.

SUMMARY

For the purposes of the present invention, the term "high-density electrodes" refers to a matrix of electrodes with a reduced interelectrode distance, currently up to 5 mm.

It is known that electromyographic signals are signals having very small power values; in fact, the measurable voltage is of the order of $\mu V$; it is therefore important that the measuring device has a high resolution of digitalization of such signals.

All known devices allow the actual number of channels used for taking a measurement to be changed in a quick and simple manner by a man skilled in the art. In fact, in such devices the number of channels to be used for taking a measurement cannot be increased beyond the number of channels for which the device has been designed.

Moreover, those devices having a large number of channels, e.g. more than thirty-two, are monolithic devices that must be placed at a distance from the patient because the dimensions of their external casing do not allow for portability or wearability by the patient. The distance between the electrode and the measuring instrument requires very long channels for transferring the electromyographic signals, which channels may then be subject to corruption due to noise, e.g. electromagnetic noise. Such noise may corrupt the electromyographic signals, thereby introducing an error and altering the reading. In addition, such measuring devices are bulky and heavy.

No devices are currently known which can manage a large number, e.g. two hundred and fifty-six, of high-resolution channels, while having a small external casing that can be held or worn by the patient.

Devices are also known which can transmit suitably conditioned data to an external processing device, e.g. a personal computer. Said connection between the processing device and the measuring device normally uses an electric cable. Said electric cable is affected by noise from the external environment, which may corrupt the data being transferred. Furthermore, from the patient safety viewpoint, the presence of a physical medium adapted to conduct electric current may be dangerous for the patient. In fact, any scattering current might be conducted by the cable itself towards the patient, which might in some cases cause serious injury to the latter.

Measuring devices are also known which are powered by the national electric mains. Such a type of power supply is dangerous for the patient. In fact, in this case there is an electric path between the patient and the power mains, where a current which is potentially dangerous for the patient might flow. In addition, the connection to the power mains introduces a quantity of wide-spectrum noise which is difficult to suppress and which might corrupt the readings.

Devices for EMG measurements are also known in which the data conditioned by the measuring device are sent to a data processing device through transmission means capable of ensuring insulation between the patient and any sources of potentially dangerous currents. Such transmission means which ensure patient safety are, for example, wireless devices or optical glass fibres. These measuring devices have to transfer small quantities of data, since they do not require any special data transmission protocols.

It is known that measurements of electromyographic signals can be taken by using different techniques for managing the signals coming from the electrodes, in particular monopolar, single differential, double differential, etc.

All devices known in the art cannot change the technique for managing the signals coming from the electrodes. As a matter of fact, measurements are taken by using only one predetermined signal management technique, for which the measuring device has been designed.

It may be useful to underline that using the devices known in art turns out to be a complex task for the operator, because such devices are normally used in the medical field, where the personnel do not have high electronic skills. As a result, the connection of the channels to the device might be made incorrectly, in which case the electromyographic signals will not be sensed properly on the patient.

All devices known in the art feature an inflexible design, in that it is impossible to change any measurement parameter, e.g. the number of channels, etc., of the original design specifications of the measuring device.

The present invention aims at solving the above-mentioned technical problems by providing a measuring device which can be assembled in a modular manner, and which is capable of varying the number of channels used for taking a measurement, while still keeping the external casing small and easily controllable by the operator.

One aspect of the present invention relates to a device for measuring electromyographic signals.

BRIEF DESCRIPTION OF THE DRAWINGS

The features and advantages of the measuring device according to the present invention will become more apparent from the following description of at least one embodiment thereof and from the annexed drawings, wherein:

FIG. 2 is a detailed block diagram of a conditioning circuit;

FIG. 3 is a detailed block diagram of a conversion circuit;

DETAILED DESCRIPTION

Figure 1:
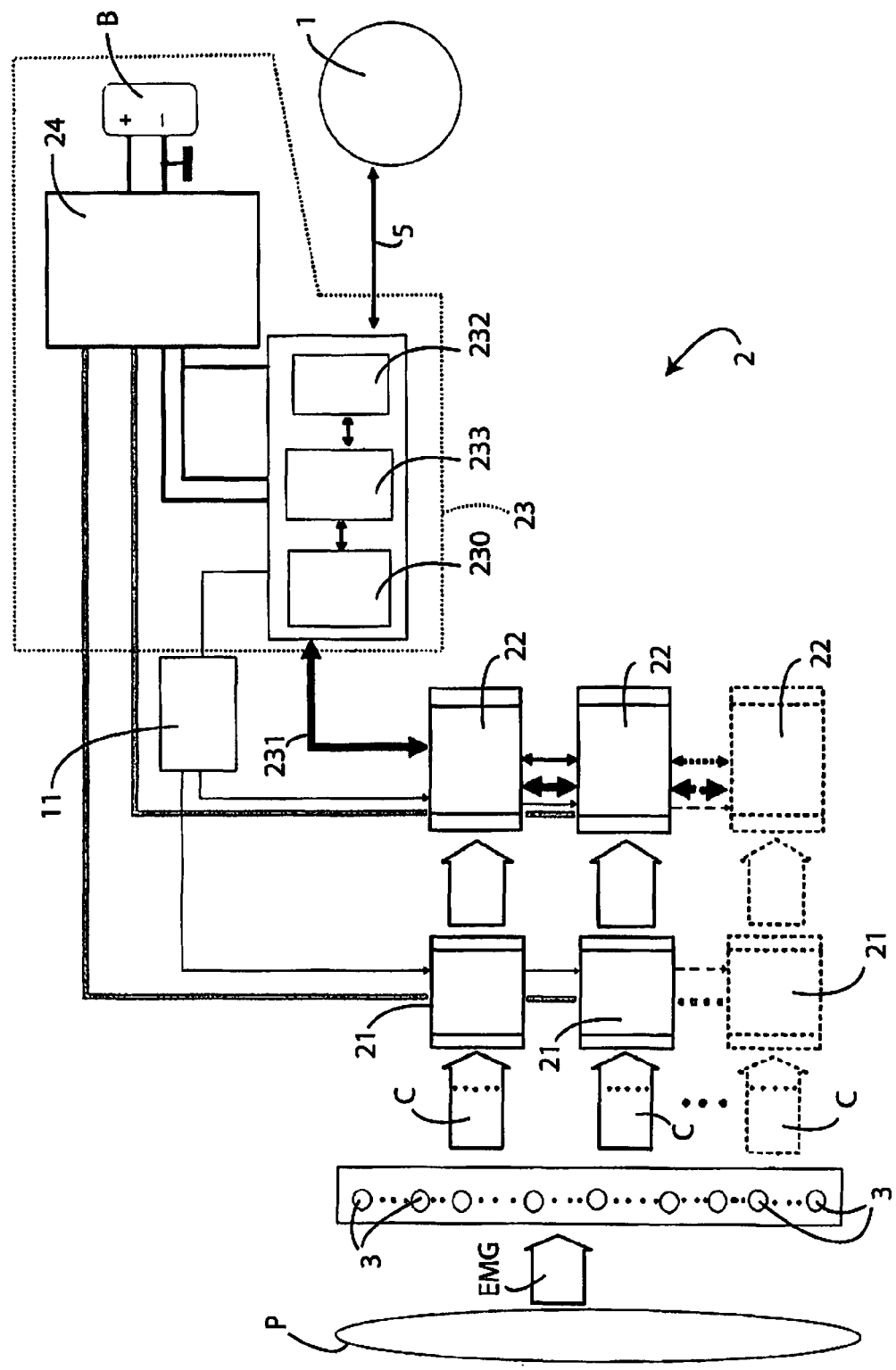
FIG. 1 is a block diagram of the measuring device according to the present invention.

With reference to the above-mentioned drawings, device 2 for measuring electromyographic signals is adapted to receive, through a plurality of channels "C", a plurality of electromyographic signals "EMG" sensed by a plurality of electrodes 3 arranged on a portion of the human body of a patient "P", preferably in a high-density configuration.

Said device 2 comprises a conditioning circuit 21, adapted to suitably condition the analog electromyographic signals; a conversion circuit 22, adapted to convert into digital form the signals conditioned by said conditioning circuit 21; a transmission circuit 23, adapted to transmit the signals digitalized by conversion circuit 22 to a central control unit 1, e.g. a personal computer, which in turn is adapted to process the received data. Said central control unit 1 is adapted to receive the data relating to signals "EMG", store them into memory media, preferably non-volatile memory media, and create graphs where it is possible, for example, to determine the position of one or more nervous terminations or muscular traumas of patient "P", etc.

The processing of the data relating to signals "EMG" may be carried out either in real time or subsequently, after having completed the measurement step on patient "P".

Said device 2 further comprises an external casing 20, adapted to enclose a plurality of electronic boards on which said circuits (21, 22, 23) have been engraved;

In addition, device 2 comprises at least one battery "B", enclosed in external casing 20 and adapted to supply power to the electric circuits included in device 2 itself. Preferably, said battery "B" has the following specifications: 6V and 2000 mAh.

Channels "C", preferably consisting of impedance-type electric cables, are connected at one end to respective electrodes 3 and at the opposite end to device 2. In particular, said channels "C" are connected to conditioning circuit 21 through at least one connector 26 provided on at least one external face of external casing 20.

Said conditioning circuit 21 can be assembled in a modular manner, by establishing a cascade connection of one or more independent conditioning circuits 21, in order to vary the number of channels through which electromyographic signals "EMG", measured on the skin of the patient "P", are received.

Said conversion circuit 22 can be assembled in a modular manner, by connecting in parallel one or more independent conversion circuits 22, depending on the number of conditioning circuits 21, in order to vary the number of channels "C" through which electromyographic signals "EMG" are received.

Said one or more conditioning circuits 21 and said one or more conversion circuits 22 appropriately overlap at least partially in order to limit the dimensions of measuring device 2 and hence of said external casing 20, thus ensuring wearability thereof on patient "P".

For the purposes of the present invention, the expression "the circuits suitably overlap" means that the electronic circuits, even though they overlap at least partially, do not interact electromagnetically with each other, thereby avoiding any problems due to mutual electromagnetic interference. The absence of any electromagnetic interaction between the circuits is also dependent on the structural shape thereof, as is known by the man skilled in the art.

Said connectors 26 may be multi-way connectors, e.g. thirty-three-way connectors, having small dimensions and allowing to quickly connect a plurality of channels "C" to device 2. Such a type of connector can be used because channels "C" have a short longitudinal extension compared with prior-art channels, which is due to the fact that device 2 is placed in the proximity of patient "P", preferably worn by the patient him/herself, and hence near electrodes 3. Furthermore, the short length of such channels makes it less likely for signal "EMG" to be corrupted by external noise, e.g. electromagnetic noise.

In a first embodiment, each conditioning circuit 21 is engraved on an independent electronic board, and each conversion circuit 22 is engraved on an independent electronic board. Such boards can be suitably overlapped on each other in order to reduce the overall dimensions of device 2.

The electronic boards, supporting each at least one conditioning circuit 21 and being appropriately interconnected in cascade, make device 2 of the present invention become modular; in fact, in device 2 it is possible to vary the number of channels "C" by changing the number of cascade-connected conditioning circuits 21.

Likewise, the electronic boards supporting each at least one conversion circuit 22 and being appropriately interconnected electrically with each other, also make device 2 of the present invention become modular.

Preferably, at least one conditioning circuit 21 is associated with each conversion circuit 22; preferably, the number of conversion circuits 22 equals the number of conditioning circuits 21 comprised in device 2 according to the present invention.

In a second equivalent embodiment, conditioning circuit 21 and conversion circuit 22 are engraved on a common electric board. Said circuits may partially overlap, e.g. on multilayer boards.

Each conditioning circuit 21 can condition electromyographic signals "EMG" coming from at least thirty-two channels "C" connected to as many electrodes 3. Moreover, as shown in FIG. 2, conditioning circuit 21 comprises, for each channel "C" associated therewith, at least one amplifier 211 adapted to amplify input signal "EMG", and at least one filter (212', 212") adapted to filter predetermined frequency components of signal "EMG".

The first stage of the conditioning circuit is amplifier 211, which has a constant gain over the whole band of signals "EMG". Said amplifier may be implemented in an instrumentation amplifier configuration, known to the man skilled in the art.

Preferably, said amplifier 211 is a low-noise amplifier with its input stage in chopper configuration, for increased immunity to low-frequency noise, in particular to flicker noise. The above-mentioned configuration further reduces the common-mode drifts of the signal EMG, thereby increasing the efficiency of the technique for removing the common-mode component of signal "EMG".

Preferably, conditioning circuit 21 comprises a first high-pass filter 212' and a second low-pass filter 212".

Said first high-pass filter 212' is adapted to eliminate the low-frequency components of signal "EMG", in particular the direct component of the signal. Said filter is preferably arranged in cascade with said amplifier 211. Preferably, said first filter 212' is a passive filter, implemented through an RC network, of at least the second order.

Said second low-pass filter 212" is adapted to reduce the high-frequency components of signal "EMG", thus making the signal wholly differential by eliminating the common-mode component of signal "EMG".

Said second filter 212" is preferably implemented by means of an active filter, e.g. of the second order.

Said second filter 212" is preferably the last stage of conditioning circuit 21, before conditioned signals "EMG" are sent to conversion circuit 22.

Each conditioning circuit 21 is also adapted to automatically change the measuring configuration among monopolar, single differential and other configurations for measuring electromyographic signals "EMG", through a plurality of switches 25.

Said plurality of switches 25 can vary the path of signals "EMG" inputted to amplifiers 211, so as to allow measuring the same signals "EMG" in different measuring configurations.

Each one of said switches 25 is preferably implemented by using CMOS SPTD technology.

For the purposes of the present invention, the term SPTD relates to a single-pole switch adapted to switch between two contacts.

Said plurality of switches 25 are controlled by at least one management unit 11. Said management unit 11 is adapted to control the switching of said plurality of switches 25 depending on the measuring configuration selected by the operator.

The selection of one measuring configuration or another can be done, in a first embodiment, through an electromechanic or electronic selector (not shown).

Each conversion circuit 22 can carry out a direct conversion of the electromyographic signals "EMG" at high resolution. For example, as shown in FIG. 3, each conversion circuit 22 comprises a plurality of sampling circuits 221, each adapted to sample one conditioned electromyographic signal "EMG" coming from conditioning circuit 21; and at least one conversion device 222, adapted to convert signals "EMG" from analog to digital.

Preferably, the resolution of said conversion circuit 22 is of at least 24 bits on a dynamics of 5V at most. In this example, the associated resolution of the least significant bit of the converted signal will be 300 nV.

Signals "EMG" transferred from conditioning circuit 21 to conversion circuit 22 are driven in a differential manner, in order to maximize the quality of the digital conversion of signals "EMG" by increasing the signal dynamics and the signal-to-noise ratio.

Said plurality of sampling circuits 221 are adapted to carry out an oversampling operation on signals "EMG" for the purpose of reducing the aliasing effect. Such an effect may be, in fact, detrimental for the conversion, in that errors may be introduced into the converted signals. Preferably, the oversampling is carried out at a frequency which is at least sixty-four times higher than the maximum frequency of signal "EMG" conditioned by conditioning circuit 21. Preferably, the sampling frequency is 2.4 kHz or 2.4 $k_{sps}$.

Furthermore, said plurality of sampling circuits 221 carry out a simultaneous sampling operation on all signals "EMG" conditioned by said at least one conditioning circuit 21, thereby avoiding sampling time variations among the various channels.

In fact, the signals sampled by sampling circuits 221 are sent directly to at least one conversion device 222. This allows to avoid using one multiplexer device and one sample and hold circuit for each channel for the cyclic selection of the channel to be converted. The solution shown herein maximizes conversion speed and eliminates any signal conversion errors caused by time latencies due to the step of selecting the channel to be converted.

Each conversion device 222 can convert at least one signal "EMG", suitably sampled by sampling circuit 221, into at least one digital signal on at least 24 bits.

Said conversion device 222 can execute a simultaneous conversion on a plurality of channels, preferably thirteen, by implementing a $\Delta\Sigma$ modulation of at least the first order, which can carry out a modulation on digitalized signal "EMG" and then demodulate it in order to obtain a digital signal with reduced components of any noise or disturbances. Said at least partial reduction of noise and disturbances mainly occurs during $\Delta\Sigma$ demodulation.

Preferably, said conversion device 222 also provides digital filtering, e.g. linear, of converted signals "EMG".

For the purposes of the present invention, the process of conversion through $\Delta\Sigma$ modulation will not be described in detail herein, since it is known to those skilled in the art.

Said transmission circuit 23 is adapted to receive the digital data coming from said one or more conversion circuit 22 and to transmit them to said control unit 1 through communication means 5 immune from conducted or radiated electromagnetic noise.

The data coming from said one or more conversion circuits 22 are sent to the transmission circuit 23, preferably through at least one full-duplex serial bus 231, preferably a synchronous one, in order to ensure a simultaneous and bidirectional data exchange.

An SPI communication system is preferably implemented on said bus 231. For the purposes of the present invention, the SPI bus will not be described in detail herein, since it is known to those skilled in the art.

Figure 4:
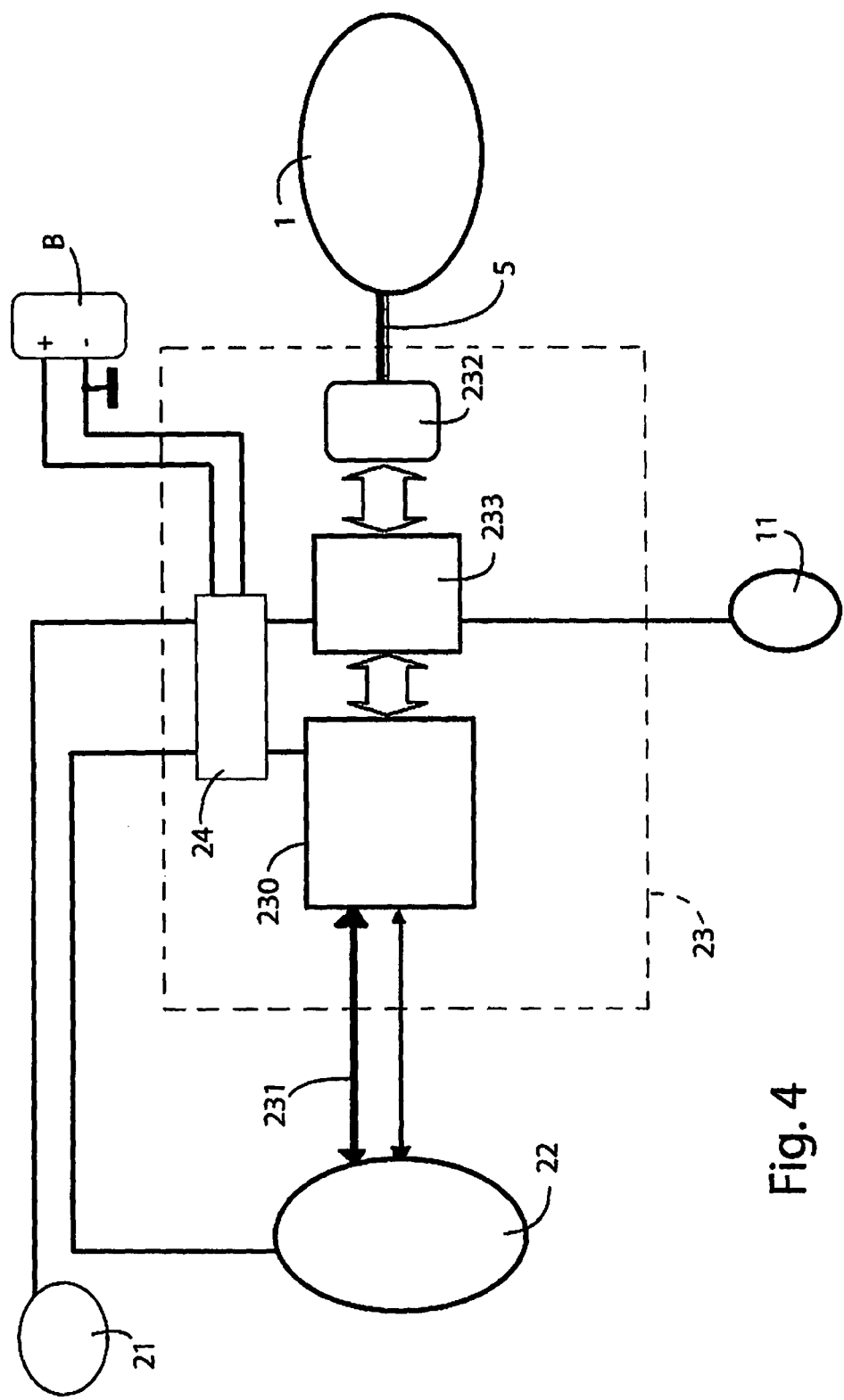
FIG. 4 is a detailed block diagram of the transmission circuit.

As shown by way of example in FIG. 4, transmission circuit 23 comprises a buffering circuit 230 adapted to temporarily store the input data, and a transmission protocol implementation circuit 233 capable of preparing the data, so that they can be transferred to central control unit 1.

In said buffering circuit 230, the data coming from at least one conversion circuit 22 are temporarily stored in a volatile memory medium, to be then transmitted to central control unit 1. In particular, said temporarily stored data are sent to the transmission protocol implementation circuit 233.

Said transmission protocol implementation circuit 233 can prepare the data, e.g. by organizing them into data packets, so that they can be transferred to central control unit 1 in accordance with a predetermined transmission protocol. By way of example, one possible transmission protocol is an Ethernet protocol operating at at least 10 Mbps, preferably a 10/100 transmission protocol. For the purpose of the present invention, the 10/100 Ethernet protocol will not be described in detail herein, since it is known to those skilled in the art.

Said transmission circuit 23 comprises a transceiver 232 adapted to transmit the data, digitalized by conversion circuit 22 and suitably organized by the transmission protocol implementation circuit 233 depending on the communication protocol employed, to central control unit 1, and to receive any data from the same central control unit 1 which may be useful, for example, to management unit 11.

Said communication means 5 allow signals "EMG", sent by said transceiver 232, to be transmitted to central control unit 1, preferably at a speed of at least 3 Mbps.

In a first configuration, said communication means 5 utilize an optical fibre, e.g. a plastic optical fibre. Such a solution allows to ensure electric insulation between the patient, to whom measuring device 2 is applied, and central control unit 1, thereby complying with electric safety regulations such as, for example, EN60601. In this configuration, transceiver 232 is an optical transceiver adapted to send optical signals through, for example, an optical laser, and to receive optical signals from central control unit 1 through an optical receiver. The use of a communication means 5 consisting of plastic optical fibre allows transmitting data at a speed of up to 1 Gbps.

The use of plastic optical fibre allows reducing the costs of communication means 5 itself. In fact, in addition to being normally less expensive than glass optical fibre, such optical fibres do not require any special cutting to ensure light conduction. Furthermore, plastic optical fibres are resistant to stress such as, for example, bending at small angles of curvature, which glass optical fibres could not withstand because such angles might cause it to break and because such bending would imply an almost total attenuation of the transmitted signal.

In a second equivalent configuration, said communication means 5 utilize a wireless connection. Such a solution allows to ensure electric insulation between the patient, to whom measuring device 2 is applied 2, and central control unit 1.

In this configuration, transceiver 232 is a radio transceiver comprising a transceiver antenna.

The use of a wireless connection allows reducing the costs because no connection cables are required between measuring device 2 and central control unit 1.

Transmission circuit 23 further comprises a power supply 24 adapted to generate a plurality of predetermined voltages, which in turn is supplied by said at least one battery "B" with voltage values suitable for supplying the correct voltage level to circuits (21, 22, 23) comprised in device 2.

Preferably, said power supply 24 can output the following voltages:
- a dual supply voltage for powering conditioning circuits 21;
- a fully differential supply voltage for powering sampling circuits 221;
- a low-noise reference voltage having a constant and accurate level, for the digital conversion carried out by conversion devices 222;
- a first voltage for powering conversion devices 222;
- a second voltage for powering transmission circuit 23;
- a third voltage for powering the data transmission devices included in communication means 5.

Preferably, transmission circuit 23 is implemented through a programmable circuit, e.g. an FPGA circuit capable of implementing very complex circuits while taking up very little space.

In particular, buffering circuit 230, transmission protocol circuit 233, power supply 24 and management unit 11 are implemented by appropriately programming said programmable circuit.

Preferably, said programmable circuit is implemented by means of low-consumption electronic devices, such as, for example, logic ports. In fact, device 2 according to the present invention only requires an instantaneous current consumption not exceeding, for example, 350 mA.

Management unit 11 included in measuring device 2 can communicate with central control unit 1 in order to transfer and receive information relating to device 2. Central control unit 1 can transfer useful information to management unit 11, e.g. the number of conditioning circuits 21 and conversion circuits 22 respectively arranged in cascade, the measuring configuration to be used for the next measurements of signals "EMG", which can then manage the plurality of switches 25 accordingly. Furthermore, said management unit 11 is adapted to monitor circuits (21, 22, 23) included in device 2 according to the present invention, and to signal any malfunctions thereof to the central control unit.

In a first embodiment, management unit 11, while transferring the data relating to signals "EMG", also transfers information about the configuration of device 2 over the same communication means 5 used for transferring digitalized signals "EMG". Such information is exchanged during a step of configuring device 2. Said configuration step can be carried out prior to each measuring campaign on a patient "P".

In a second embodiment, management unit 11 communicates with central control unit 1 through a dedicated connection. Said dedicated connection is a second communication means (not shown), e.g. an electric cable. The information about device 2 is exchanged in a step preceding or following the measurement step carried out on patient "P", in particular in a condition wherein the same device 2 is not being worn by or has not been placed in the proximity of patient "P", and electrodes 3 have not been applied to the patient and connected to the same device 2.

In one embodiment (not shown) of device 2 according to the present invention, transmission circuit 23 comprises a storage circuit adapted to store into a non-volatile memory medium at least a portion of the data coming from conversion circuits 22.

Figure 5:
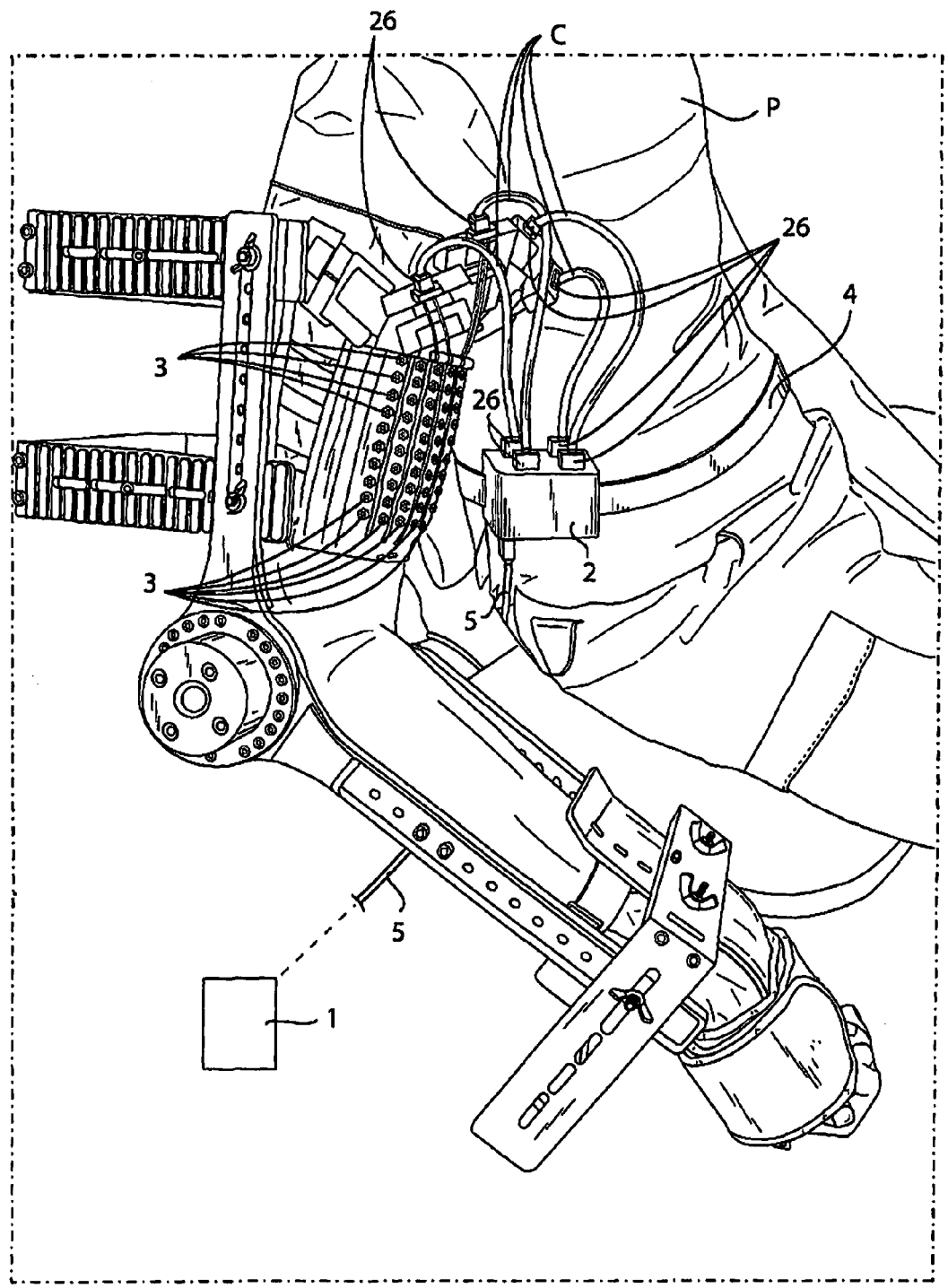
FIG. 5 shows the device according to the present invention in one of its possible applications, in particular when applied to a patient "P" for measuring action potentials with high-density electrodes.

Device 2 according to the present invention is placed in the proximity of patient "P", e.g. it is worn by the patient by means of at least one fastening element 4. In a first embodiment, said fastening element 4 is, for example, a belt secured to external casing 20 and tightened around a portion of the body of patient "P", e.g. an arm, a leg, or the chest, as shown by way of example in FIG. 5.

In a second equivalent embodiment, said at least one fastening element 4 is, for example, a garment. Said garment, which is adapted to be worn by patient "P", comprises a casing adapted to accommodate said device 2. Said fastening element 4 is, for example, a jersey, a pair of trousers, a glove, etc.

In a third equivalent embodiment, said at least one fastening means 4 is a portion of adhesive material, e.g. velcro, applied to a face of external casing 20, to be attached to the clothes of patient "P".

Measuring device 2 is implemented in such a way as to be immune from conducted or radiated electromagnetic interference coming from the external environment. Preferably, device 2 comprises at least one metal structure, appropriately connected to the ground point and adapted to shield circuits (21, 22, 23) against external electromagnetic waves. Said metal structure may be comprised in or secured to external casing 20 of device 2. Channels "C" may possibly be fitted with a ferrite element adapted to eliminate any electromagnetic noise conducted by the same channels "C".

Device 2 according to the present invention allows taking measurements on a patient "P" at high resolution with a large number of input channels "C", thereby reducing the sources of error that might affect the reading, as well as any electromagnetic interference. Furthermore, said device can be worn by the patient, thus reducing the length of channels "C" and hence the attenuation undergone by signal "EMG" as it is being transmitted over channel "C".

In addition, device 2, being powered by means of at least one battery "B", is safe for patient "P" because there is no physical electrical connection between device 2 and a power source, which may be potentially dangerous for the patient.

The circuits included in device 2 are adapted to reduce power consumption, thus allowing for measurement campaigns lasting up to six consecutive hours.

Said at least one battery "B", once discharged, may be either replaced or recharged by means of a battery charger (not shown) to be connected to device 2 when the latter is not taking any measurements on a patient "P".

The modular construction of device 2 allows varying the number of channels "C" to be used for a measurement by changing the number of conditioning circuits and conversion circuits.

The present invention covers all possible combinations of each device with the remaining devices in accordance with the different embodiments described herein.

NUMERIC REFERENCES

1 Central control unit
11 Management unit
2 Device for measuring electromyographic signals
20 External casing
21 Conditioning circuit
211 Amplifier
212' First high-pass filter
212" Second low-pass filter
22 Conversion circuit
221 Sampling circuits
222 Conversion device
23 Transmission circuit
230 Buffering circuit
231 Bus
232 Transceiver
233 Transmission protocol implementation circuit
24 Power supply
25 Switch
26 Connectors
3 Electrodes
4 Fastening element
5 Communication means
B Battery
C Channels
EMG Electromyographic signals
P Patient

The invention claimed is:

1. Device for measuring electromyographic signals, configured for receiving, through a plurality of channels, a plurality of electromyographic signals sensed by a plurality of electrodes arranged on a portion of the body of a patient; said device comprising:
 a conditioning circuit, for conditioning analog electromyographic signals;
 a conversion circuit, for converting data of the signals conditioned by said conditioning circuit into digital form;
 a transmission circuit, for transmitting the data digitalized by the conversion circuit to a central control unit for processing the data;
 an external casing, configured for enclosing a plurality of electronic boards on which said circuits have been engraved;
wherein:
 said conditioning circuit is configured for modular assembly, comprising a parallel connection of independent conditioning circuits to vary the number of channels through which electromyographic signals are received;
 said conversion circuit is configured for modular assembly, said conversion circuit having one or more independent conversion circuits connected in parallel, depending on the number of conditioning circuits to vary the number of channels through which electromyographic signals are received;
 said one or more conditioning circuits and said one or more conversion circuits overlap at least partially to limit dimensions of said external casing;
 said device is configured for being worn by the patient, by at least one fastening element.

2. The device according to claim 1, comprising at least one battery, which is enclosed in the external casing and is adapted to supply power to the electric circuits included in the device.

3. The device according to claim 2, wherein each conditioning circuit, which comprises, for each channel, at least one amplifier and at least one filter is configured to condition the electromyographic signals coming from at least thirty-two channels connected to as many electrodes.

4. The device according to claim 3, wherein the number of conversion circuits equals the number of conditioning circuits.

5. The device according to claim 3, wherein each conversion circuit, which comprises a plurality of sampling circuits and at least one conversion device is configured to carry out a direct conversion of the electromyographic signals, at a resolution of at least 24 bits on a dynamics of 5V at most.

6. The device according to claim 5, wherein said plurality of sampling devices are adapted to carry out, in a simultaneous manner, an oversampling operation on the conditioned signals.

7. The device according to claim 3, wherein each conditioning circuit is adapted to automatically change a measuring configuration among monopolar, single differential and other configurations for measuring electromyographic signals, through at least one switch.

8. The device according to claim 2, wherein said transmission circuit comprises a buffering circuit for temporarily storing the input data; a transmission protocol implementation circuit capable of preparing the data so that the data can be transferred to the central control unit through a device for communicating shielded from conducted or radiated electromagnetic noise.

9. The device according to claim 8, wherein said device for communicating is a plastic optical fibre.

10. The device according to claim 8, wherein said device for communicating is a wireless connection.

11. The device according to claim 2, wherein the conditioning circuit and the conversion circuit are comprised in a single electronic board.

12. The device according to claim 2, wherein the electrodes are arranged on a patient in a high-density configuration.

13. The device according to claim 2, comprising a power supply for generating a plurality of stable voltages from said at least one battery, the voltage values being suitable for supplying the correct voltage level to the circuits.

14. The device according to claim 2, wherein the device comprises a management unit for:

communicating with the central control unit to transfer and receive information about the device;

monitoring the circuits and signal malfunctions of said circuits to the central control unit.

15. The device according to claim 1, wherein:

said transmission circuit transmits the data digitalized to said control unit through a device for communicating shielded from conducted or radiated electromagnetic noise;

the data from said one or more conversion circuits are sent to the transmission circuit through at least one full-duplex serial bus.

16. A device for measuring electromyographic signals, configured for receiving through a plurality of channels, a plurality of electromyographic signals adapted to be sensed by a plurality of electrodes arranged on a portion of the body of a patient; said device comprising:

a conditioning circuit for conditioning analog electromyographic signals;

a conversion circuit for converting the signals conditioned by said conditioning circuit into digital form;

a transmission circuit, for transmitting the signals digitalized by the conversion circuit to a central control unit for processing data;

an external casing, configured for enclosing a plurality of electronic boards on which said circuits have been engraved;

wherein:

said conditioning circuit is configured for modular assembly, the conditioning circuit comprising a parallel connection of independent conditioning circuits to vary the number of channels through which electromyographic signals are received;

said conversion circuit is configured for modular assembly and for being connected in parallel one or more independent conversion circuits, depending on the number of conditioning circuits to vary the number of channels through which electromyographic signals are received;

said one or more conditioning circuits and said one or more conversion circuits overlap at least partially to limit dimensions of said external casing;

said transmission circuit transmits the signals digitalized to said control unit through a device for communicating shielded from conducted or radiated electromagnetic noise;

the signals converted into digital form from said one or more conversion circuits are sent to the transmission circuit through at least one full-duplex serial bus.

\* \* \* \* \*